US012663409B2

(12) United States Patent
Rahman et al.

(10) Patent No.: US 12,663,409 B2
(45) Date of Patent: Jun. 23, 2026

(54) SENSOR AND METHOD FOR DETERMINING FRACTIONS OF OIL, WATER, AND SOLIDS IN DRILLING FLUID IN REAL TIME

(71) Applicant: Baker Hughes Oilfield Operations LLC, Houston, TX (US)

(72) Inventors: Syed Ehsanur Rahman, Conroe, TX (US); Ian L. Everhard, The Woodlands, TX (US); Reza Ettehadi Osgouei, Spring, TX (US); Nils Kaageson-Loe, Claremore, OK (US); Aswath Krishnan, Spring, TX (US)

( * ) Notice: Subject to any disclaimer, the term of this patent is extended or adjusted under 35 U.S.C. 154(b) by 330 days.

(21) Appl. No.: 18/475,439

(22) Filed: Sep. 27, 2023

(65) Prior Publication Data

US 2025/0102489 A1 Mar. 27, 2025

(51) Int. Cl.
| *G01N 33/28* | (2006.01) |
| *G01N 9/32* | (2006.01) |
| *G01N 27/06* | (2006.01) |
| *G01N 27/74* | (2006.01) |

(52) U.S. Cl.
CPC .......... *G01N 33/2823* (2013.01); *G01N 9/32* (2013.01); *G01N 27/06* (2013.01); *G01N 27/74* (2013.01)

(58) Field of Classification Search
CPC ........ G01N 33/2823; G01N 9/32; G01N 7/06; G01N 27/74
See application file for complete search history.

(56) References Cited

U.S. PATENT DOCUMENTS

| 2005/0229716 A1 | 10/2005 | Unsworth et al. |
| 2013/0285677 A1 | 10/2013 | Hammer |
| 2018/0080295 A1 | 3/2018 | Newman et al. |

(Continued)

FOREIGN PATENT DOCUMENTS

| EP | 1250573 B1 | 4/2011 |
| EP | 1546695 B1 | 6/2014 |

OTHER PUBLICATIONS

Direct Industry ABB "In-line conductivity meter ACA592"; https://www.directindustry.com/prod/abb-measurement-analytics/product-56271-433021.html; printed from the Web; 3 pages.

(Continued)

*Primary Examiner* — Kristina M Deherrera
*Assistant Examiner* — Jean F Morello
(74) *Attorney, Agent, or Firm* — Baker Hughes Company

(57) ABSTRACT

An apparatus for estimating an oil, water, and solids fraction of a drilling fluid includes a conduit containing the drilling fluid, an electromagnetic sensor in communication with the drilling fluid that senses a combined water and solids fraction, and at least one of a conductivity sensor or a density sensor, each in communication with the drilling fluid. The apparatus also includes a processing system determining the fraction of oil, water, and solids in the drilling fluid using the combined water and solid fraction and at least one of the conductivity value from the conductivity sensor or the density value from the density sensor and a controller coupled to the processing system, the controller having an output coupled to a drilling fluid additive control device controlling an additive to be added to the drilling fluid based on the fraction of oil, water, and solids of the drilling fluid.

14 Claims, 3 Drawing Sheets

(56) References Cited

U.S. PATENT DOCUMENTS

| | | |
|---|---|---|
| 2020/0209193 A1 | 7/2020 | Swett et al. |
| 2023/0024801 A1* | 1/2023 | Ma ........................... G01V 3/28 |
| 2023/0149869 A1 | 5/2023 | Smith |
| 2023/0220760 A1 | 7/2023 | Benson et al. |

OTHER PUBLICATIONS

Emerson Electric Co. "Coriolis Flow Meters for Mass, Volume, & Density"; https://www.emerson.com/en-us/automation/measurement-instrumentation/flow-measurement/coriolis-flow-meters-for-mass-volume-density-measurement; printed from the Web; 8 pages.
Endress + Hauser "Coriolis mass flowmeters"; 1. https://www.us.endress.com/en/field-instruments-overview/flow-measurement-product-overview/coriolis-mass-flowmeters; printed from the Web; 11 pages.
Hammertech AquaField; https://hammertech.no/aquafield-details/; printed from the Web; 9 pages.
International Search Report and Written Opinion; PCT/US2024/047192; Korean Intellectual Property Office; Mailed Dec. 19, 2024; 10 pages.
Krohne Optimass 1400; https://krohne.com/en/products/flow-measurement/flowmeters/coriolis-mass-flowmeters/optimass-1400; printed from the Web; 3 pages.

* cited by examiner

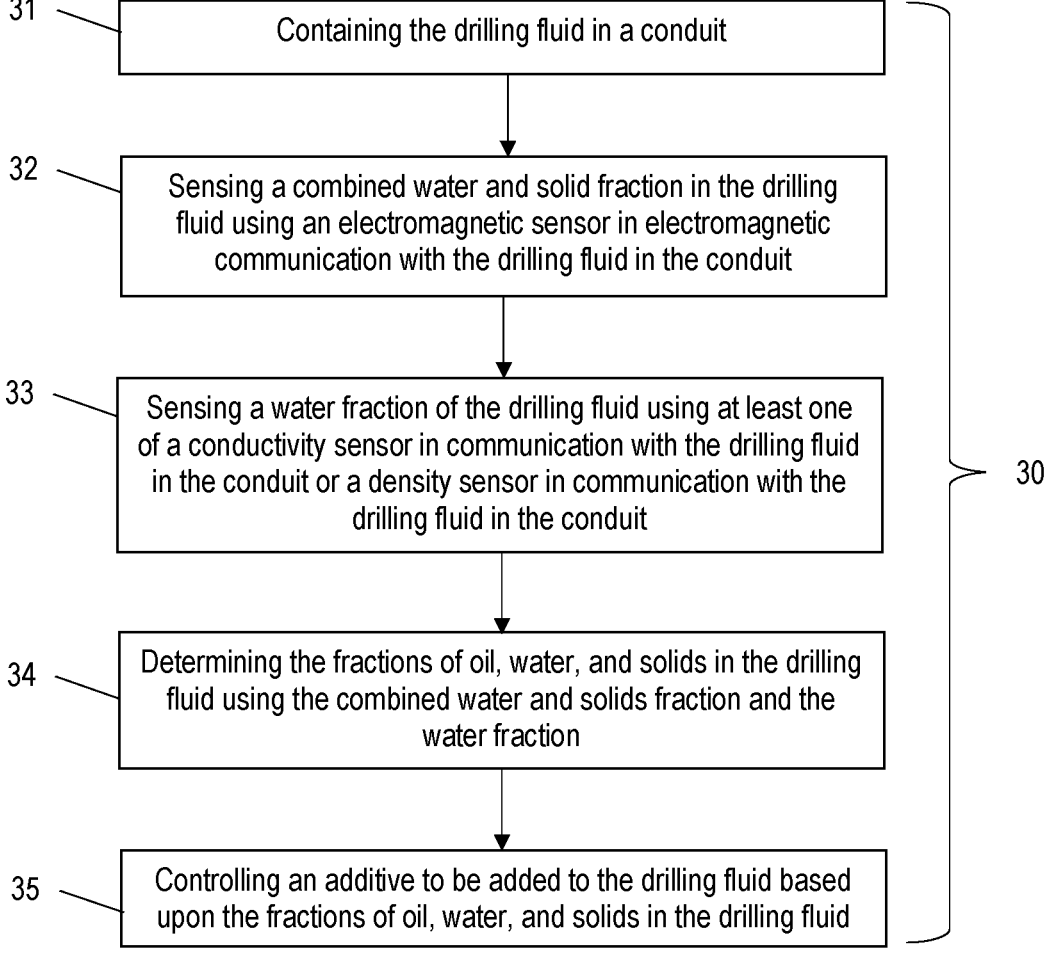

31 — Containing the drilling fluid in a conduit

32 — Sensing a combined water and solid fraction in the drilling fluid using an electromagnetic sensor in electromagnetic communication with the drilling fluid in the conduit 33 — Sensing a water fraction of the drilling fluid using at least one of a conductivity sensor in communication with the drilling fluid in the conduit or a density sensor in communication with the drilling fluid in the conduit 34 — Determining the fractions of oil, water, and solids in the drilling fluid using the combined water and solids fraction and the water fraction 35 — Controlling an additive to be added to the drilling fluid based upon the fractions of oil, water, and solids in the drilling fluid

SENSOR AND METHOD FOR DETERMINING FRACTIONS OF OIL, WATER, AND SOLIDS IN DRILLING FLUID IN REAL TIME

BACKGROUND

This disclosure relates generally to oilfield equipment for evaluating drilling fluid also referred to as drilling mud and more particularly to sensors and methods for determining the fraction of oil, water, and solids inline and in real time in the drilling fluid, which may also be referred to as so-called drilling mud.

Knowledge of certain parameters of drilling fluid is useful to efficiently drill subsurface wells and prevent problems from occurring. For example, with oil-based mud keeping a specified oil-water ratio is useful for maintaining mud and invert emulsion stability. Also, knowing the ratio of oil and water helps to detect an influx of water.

Having certain percentages of solids is also useful for drilling mud. For example, having High Gravity Solids (HGS) helps to increase mud weight which gives hydrostatics balance and helps to prevent blowout. As another example, Low Gravity Solids (LGS) can be generated from drilling cuttings and having a certain percentage of LGS is useful for carrying cuttings to the surface and mud stability.

Maintaining the correct fraction of solids in drilling mud can lead to drilling efficiency as not having the correct amount of solids might require more dilution of drilling mud which can cause use of excessive amounts of oil and chemicals and their associated costs. Thus, being able to know correct quantity of drilling mud components can help to reduce cost and environmental impacts.

With respect to water-based drilling mud, keeping a certain percentage of oil is useful for having some lubrication characteristics of the mud resulting in a decreased co-efficient of friction which helps to reduce heat, erosion and damage of tools.

Displacement occurs when drillers switch from drilling fluids to drill in fluid or drill in fluid to completion fluid. Hence, it is useful to know to know exactly when one type of mud is replaced by the other type completely.

Presently, a retort procedure is used to determine fractions of drilling fluid components. The retort procedure takes two hours or more to perform and generally requires heating a sample to 950° F., which requires implementation of certain safety procedures. Hence, it would be well received in the drilling industry if methods and apparatuses were developed to determine fractions of components of drilling fluid quickly and efficiently.

BRIEF SUMMARY

An embodiment of an apparatus for estimating a fraction of oil, water, and solids of a drilling fluid, the apparatus including a conduit containing the drilling fluid, an electromagnetic sensor in electromagnetic communication with the drilling fluid in the conduit, the electromagnetic sensor comprising a coil and electronics coupled to the coil, the electronics generating current in the coil inducing eddy currents in the drilling fluid and measuring an energy loss due to the eddy currents, the energy loss being correlated to a combined water and solids fraction, at least one of (i) a conductivity sensor comprising electronics coupled to a conductivity probe in conductive communication with the drilling fluid to provide a conductivity value or (ii) a density sensor comprising electronics coupled to a Coriolis sensor in communication with the drilling fluid to provide a density value, a processing system determining the fraction of oil, water, and solids in the drilling fluid using the combined water and solid fraction and at least one of the conductivity value from the conductivity sensor or the density value from the density sensor, the processing system having a first input coupled to the electromagnetic sensor, at least one of a second input coupled to the conductivity sensor or a third input coupled to the density sensor, and an output providing the fraction of oil, water, and solids, and a controller coupled to the output of the processing system, the controller having an output coupled to a drilling fluid additive control device controlling an additive to be added to the drilling fluid based on the fraction of oil, water, and solids of the drilling fluid.

An embodiment of a method for estimating an oil, water, and solids fraction of a drilling fluid, the method including containing the drilling fluid in a conduit, sensing a combined water and solid fraction in the drilling fluid using an electromagnetic sensor in electromagnetic communication with the drilling fluid in the conduit, sensing a water fraction of the drilling fluid using a conductivity sensor in communication with the drilling fluid in the conduit or a density value of the drilling fluid using a density sensor in communication with the drilling fluid in the conduit, determining the fraction of oil, water, and solids in the drilling fluid using the combined water and solid fraction and the water fraction, and controlling an additive to be added to the drilling fluid based upon the fraction of oil, water, and solids in the drilling fluid.

BRIEF DESCRIPTION OF THE DRAWINGS

The following descriptions should not be considered limiting in any way. With reference to the accompanying drawings, like elements are numbered alike:

FIG. 3 is a flowchart representation of a method for estimating fractions of components of a drilling fluid.

DETAILED DESCRIPTION

A detailed description of one or more embodiments of the disclosed apparatus and method presented herein by way of exemplification and not limitation with reference to the figures. In the figures, arrows representing conveyance of a fluid (or even a flowable solid) may include representing pipes or structures for confining a flow and may be referred to as "a conduit" herein. These arrows may also represent any associated components such as valves, pumps, and fittings needed for flowing and/or controlling the fluid. Similarly, arrows used to illustrate signal communication may represent a communication medium such as a conductor for electrical signals and/or a fiber optic for optical signals. These arrows may also represent any associated components such as connectors, splices, and/or signal devices needed for signal communication between components.

Disclosed are apparatuses and methods for estimating fractions of components of interest of drilling fluid. In particular, the components of interest are oil, water, and solids. In one or more embodiments, the fractions a presented as a percent of volume although other units may be used such as a weight percent or a ratio of one component to another component or components in non-limiting embodiments.

Figure 1:
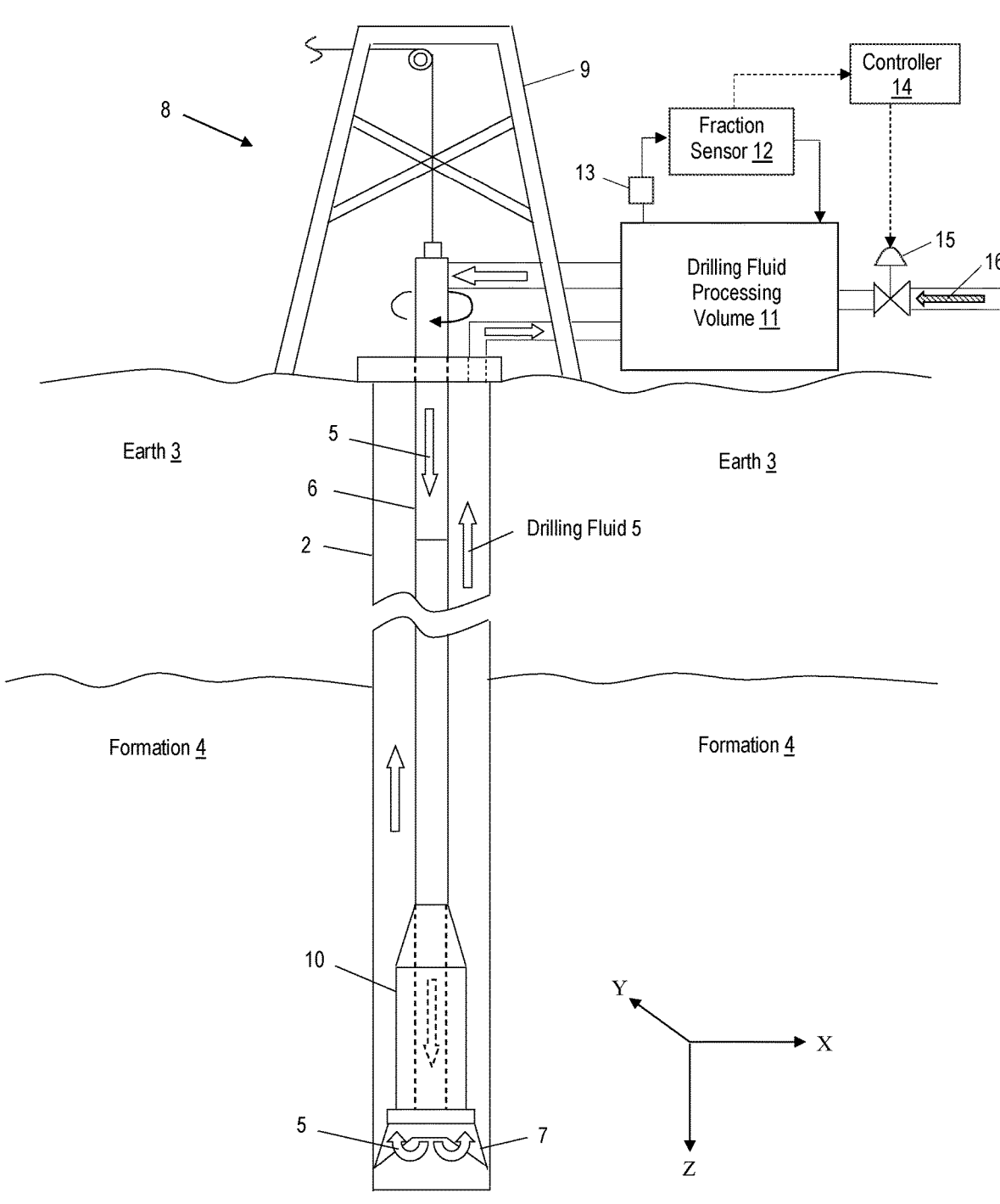
FIG. 1 illustrates a drilling system for drilling a subsurface borehole.

FIG. 1 illustrates a non-limiting embodiment of a drilling system 8. The drilling system 8 includes a drill rig 9. The drill rig 9 is configured to output energy to a drill bit 7 for drilling a borehole 2 in the earth 3 having a formation 4 that has a reservoir of hydrocarbons. For example, the drill rig 9 may be configured to rotate a drill tubular 6, such as a series of coupled drill pipes, which in turn rotates the drill bit 7 to drill the borehole 2. The drill bit 7 is disposed at a distal end of the drill tubular 6 and may be included in a bottom-hole assembly 10, which may include sensors and/or directional drilling components. Alternatively, in a coiled-tubing embodiment the drill rig 9 may be configured to pump drilling fluid 5 (also referred to as drilling mud) to a downhole mud motor (not shown) that turns the drill bit 7. In one or more embodiments, the drill rig 9 pumps the drilling fluid 5 through the drill tubular 6 to the drill bit 7 to lubricate the drill bit 7 and flush cuttings from the borehole 2.

A drilling fluid processing volume 11 is disposed at the surface of the earth 3. The drilling fluid processing volume 11 represents one or more volumes that receive the drilling fluid 5 and cuttings from the borehole 2 and/or mix additives 16 to the drilling fluid 5 before being pumped downhole.

A drilling fluid component fraction sensor 12 receives a sample of the drilling fluid 5 from the drilling fluid processing volume 11. The drilling fluid component fraction sensor 12 is configured to sense a fractional amount for each of oil, water, and solids that make up the drilling fluid 5. The fractional amounts may be referred to as ratios and in general add up to 100 percent. A sample pump 13 may be used to pump the drilling fluid 5 from the drilling fluid processing volume 11 and provide the sample to the drilling fluid component fraction sensor 12 for sensing and analysis.

The drilling fluid component fraction sensor 12 sends a signal having a fractional value for each of oil, water, and solids to a controller 14. The controller 14 is coupled to and controls a drilling fluid additive control device 15. Non-limiting examples of the drilling fluid additive control device 15 include a valve and a metering pump. The drilling fluid additive control device 15 controls an amount of a selected additive 16 that is added to the drilling fluid 5. The type of additive (e.g., water) and an amount of the additive is selected to achieve a selected percentage of each component in the drilling fluid 5 to meet a selected objective. The desired percentage of each drilling fluid component may be input into the controller 14 as one or more control setpoints. The setpoints may be entered manually or by a digital connection such as by a computer processing system. In one or more embodiments, the controller 14 implements feedback control using feedback input from the drilling fluid component fraction sensor 12. The controller 14 may implement traditional analog control algorithms such as proportional, integral, and/or derivative control or the controller may implement model-based control algorithms, neural network algorithms, machine-learning algorithms, or artificial intelligence-based algorithms as known in the art.

Figure 2:
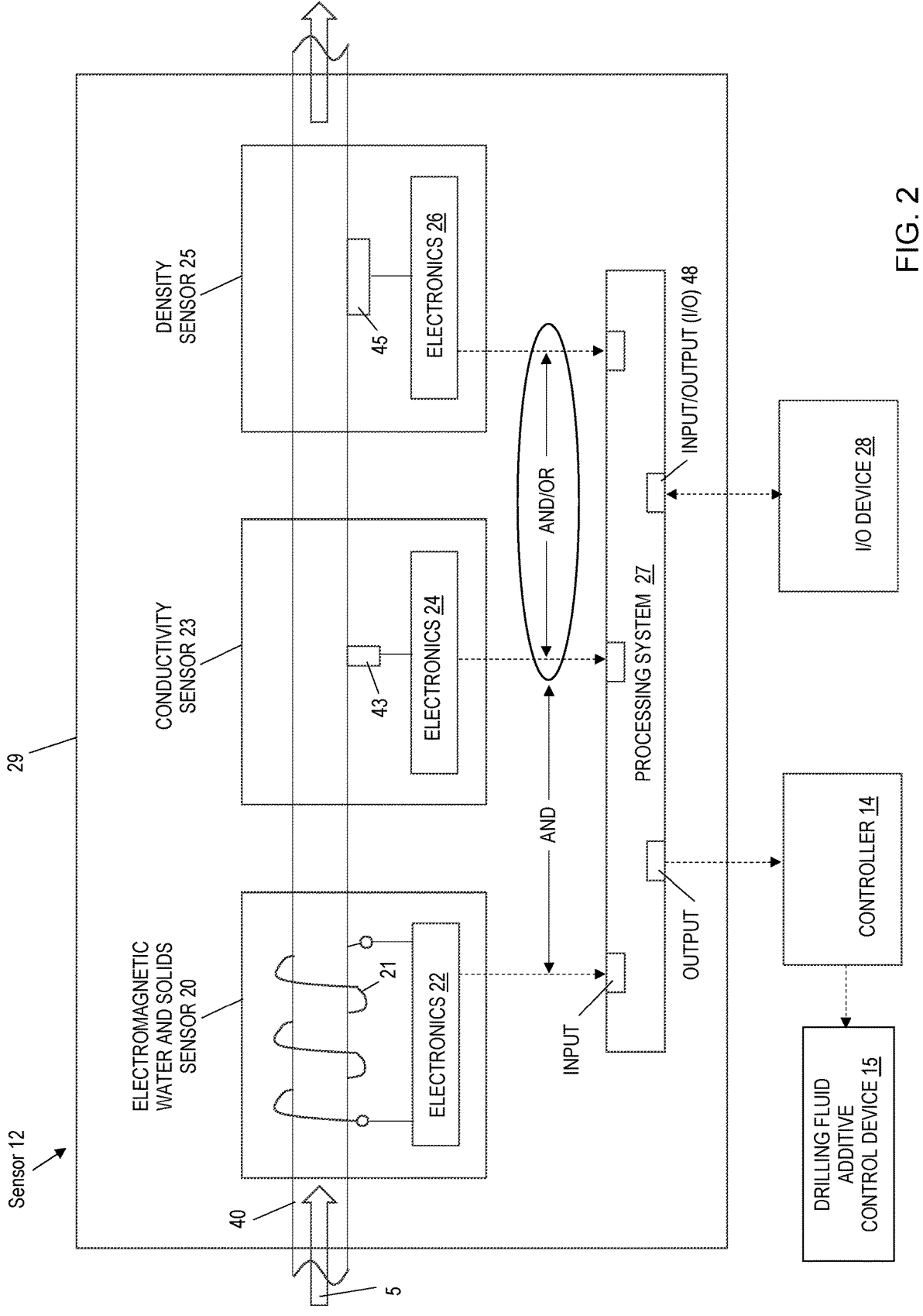
FIG. 2 depicts aspects of an apparatus for sensing fractions of components in a sample of drilling fluid.

FIG. 2 depicts aspect of the drilling fluid component fraction sensor 12 (referred to herein as the fraction sensor 12). The fraction sensor 12 includes a conduit 40 configured to direct and contain flow of the drilling fluid 5 through the fraction sensor 12. The drilling fluid 5 may flow continuously or it may be temporarily static for a selected time period to conduct a fraction measurement. Ends of the conduit 40 may include fluid connections (not shown) such as flanges to aid in connecting the sensor 12 to a source supplying the drilling fluid 5 and to a path returning the drilling fluid sample to the source or other destination.

The fraction sensor 12 includes an electromagnetic water and solids sensor 20 and at least one of a conductivity sensor 23 or a density sensor 25. Oil, water, and solids fractions can be determined (1) using the electromagnetic water and solids sensor 20 in combination with the conductivity sensor 23, referred to as Method 1, or (2) using the electromagnetic water and solids sensor 20 in combination with the density sensor 25, referred to as Method 2. The electromagnetic water and solids sensor 20 and at least one of a conductivity sensor 23 or a density sensor 25 are coupled to a processing system 27 discussed further below. When the fraction sensor 12 includes the sensors 20, 23, and 25, the fractions determined using sensors 20 and 23 can be compared to the fractions determined using the sensors 20 and 25.

A housing 29 may be used to contain and/or support components of the drilling fluid component fraction sensor 12 as illustrated in FIG. 2. For example, the sensors 20, 23 and 25 and the processing system 27 may be disposed within the housing 29. In another example, the sensors 20, 23 and 25 may be disposed within the housing 29 and the processing system 27 disposed remotely. In yet another example, each of the components 20, 23, 25, and 27 may be housed in separate housings.

The electromagnetic water and solids sensor 20 includes a coil 21 coupled to electronics 22. The electronics 22 include an amplifier circuit (not shown) for transmitting a varying current into the coil 21 to produce a varying strength magnetic field in the conduit 40. The electronics 22 also include a receiver circuit (not shown) for receiving a return signal due to the transmitted current (i.e., transmitted signal). It measures the water and solid content in the sample using a non-intrusive sensor design. The detection principle is based on a change in power loss between the transmitted and return signals due to eddy currents generated because of the varying strength magnetic field and is only influenced by the water and solid content in the sample. The current in the coil generates an eddy current in the sample that creates a magnetic field that opposes the change in the magnetic field that created it. The eddy currents then react back on the source of the magnetic field according to Lenz's law. When a conductor is exposed to a varying magnetic field, eddy currents will be induced in the water and solid. These eddy currents induce a magnetic field which opposes the original field and power is lost due to the eddy currents in the water and solid, and only in the water and solid portion of the sample. The loss of power is proportional to a sum of the water and solid content. Large amounts of water and solid will result in large amounts of energy loss and small amounts of water and solid will result in small amounts of energy loss. Eddy currents can only exist in the water and solid part of the sample, not in the oil or hydrocarbon part of the sample. Conductivity of the sample will also affect the energy loss such that highly conductive water in the sample will result in higher eddy current loss and thus a higher energy loss. Process water with low conductivity will result in a lower eddy current loss and thus a lower energy loss. Consequently, in one or more embodiments, conductivity may be measured simultaneously using the sensor 23 and compensated for. Hence, by comparing the return signal to the transmitted signal and specifically the properties of the signals related to energy loss (such as amplitude difference) the fractional amount of the combination of water and solids in the drilling fluid sample can be determined. The electromagnetic water and solids sensor 20 can be calibrated by analysis, by testing with one of or more reference samples having known fraction amount values, or by a combination of both analysis and testing. One example of the electromagnetic water and solids sensor 20 is THE AQUA-FIELD™ commercially available from HAMMERTECH® of Bergen, Norway.

The conductivity sensor 23 is configured to sense a conductivity of the sample of the drilling fluid 5 in the conduit 40. In one or more embodiments, the conductivity sensor 23 includes a conductivity probe 43 coupled to electronics 24. The conductivity probe 43 emits a microwave signal received from a transmitter circuit (not shown) in the electronics 24 directly into the drilling fluid 5. Some of the energy from the incident microwave signal will be absorbed by the drilling fluid 5 and some energy will be reflected by the drilling fluid 5. The reflected energy will be characterized by a reflected signal that will have a different amplitude and a different phase shift from the incident signal. Hence, conductivity can then be calculated for the water in the sample based on the measured amplitude attenuation and phase shift. The conductivity sensor 23 can be calibrated by analysis, by testing with one of more sample references having known conductivity values, or by a combination of both analysis and testing. One example of the conductivity sensor 23 is commercially available with THE AQUAFIELD™ from HAMMERTECH® of Norway. Another example of the conductivity sensor 20 is the In-line Conductivity Meter ACA592 commercially available from ABB Measurement & Analytics of Pennsylvania, USA.

The density sensor 25 is configured to sense a density of the sample of the drilling fluid 5 in the conduit 40. In one or more embodiments, the density sensor 25 includes a Coriolis sensor 45 coupled to electronics 26. The Coriolis sensor 45 is configured to sense density based on the Coriolis principle. In one or more embodiments, the Coriolis sensor 45 includes one or more measuring tubes which an exciter causes to oscillate. As soon as the fluid starts to flow in the measuring tube, additional twisting is imposed on this oscillation due to the fluid's inertia. The Coriolis sensor 45 detects this change of the tube oscillation in time and space as a phase difference signal. The phase difference is measured by the electronics 26 and is a direct measure of the density. The density sensor 25 can be calibrated by analysis, by testing with one of more reference samples having known fraction amount values, or by a combination of both analysis and testing. Commercially available examples of the density sensor 25 include: the OPTIMASS 1400 from KROHNE Messtechnik GmbH of Duisburg, Germany; any of several Proline Promass Coriolis flowmeters from Endress+Hauser USA; and any of several Micro Motion ELITE Coriolis Meters from Emerson Electric Company, USA.

Commercially available sensors 20, 23 and 25 may already be calibrated by the manufacturer.

The processing system 27 is configured to receive inputs from the electromagnetic water and solids sensor 20 and at least one of a conductivity sensor 23 or a density sensor 25 and to determine the fractional amounts of each of oil, water, and solids in the sample of the drilling fluid 5. The electromagnetic water and solids sensor 20 provides a fractional amount value of the combination of water and solids in the sample of the drilling fluid 5, the conductivity sensor 23 provides a conductivity value for the sample of the drilling fluid 5, and the density sensor 25 provides a density value for the sample of the drilling fluid 5.

The processing system 27 determines the fractional amounts of each of oil, water, and solids in the sample of the drilling fluid 5 using Method 1 (using inputs from sensors 20 and 23) and/or Method 2 (using inputs from sensors 20 and 25).

With respect to Method 1, the conductivity of the sample relates to an amount of water in the sample. Hence, by knowing a total sensing volume of the sample the conductivity value is a measure of the fraction of water in the sample. Thus, the processing system 27 calculates the fraction of water using the conductivity value and the known sensing volume of the sample. For example, if the known sensing volume was completely filled with water, then the measured conductivity would have a certain value. If water made up only half the volume, then the measured conductivity value would be less than the value for 100% water fill. Hence, the water fraction can be determined using the conductivity value and a conversion factor for a specific sensor configuration such as by multiplying the conductivity value by the conversion factor for example. The processing system 27 then calculates the solids fraction by subtracting the water fraction from the fraction of the combination of the water and solids together. Thus, the oil fraction is the remainder after the water and solids fractions are calculated knowing that fractions of the water+solids+oil=100%.

With respect to Method 2, this method is based on the density of the solids being greater than the density of water. The initial formulation of the drilling fluid 5 is input to the processing system 27. The initial formulation includes known fractional values for each of water, solids, and oil and an initial density value of the initial formulation of the drilling fluid. The sensed values from the electromagnetic water and solids sensor 20 and the density sensor 25 are monitored and compared to the initial formulation values. If the water and solids sensor 20 reading goes up, and the density sensor 25 reading goes down, then the change in density is attributed to an increase in the water fraction. Conversely, if the water and solids sensor 20 reading goes up, and the density sensor 25 reading also goes up, then the change in density is attributed to an increase in the solids fraction. Accordingly, the processing system 27 determines changes to the initial formulation based on changes to the readings of the water and solids sensor 20 and the density sensor 25. For example, if the initial formulation is 40% water and 20% solids, the water and solids sensor will read 60%. If later the water and solids sensor reads 62% and the density sensor 25 reads a lower value, then the lower value is attributed to an increase in the water fraction and the water fraction is determined to be 42% with solids being 20% and the remainder being oil. For another example, if later the water and solids sensor reads 62% and the density sensor 25 reads a higher value, then the higher value is attributed to an increase in the solids fraction and the solids fraction is determined to be 22%. with water being 40% and the remainder being oil. Hence, the processing system 27 determines that changes to the initial formulation of the drilling fluid 5 is based on changes in sensed density with a decrease in sensed density being attributed to an increase in the water fraction and an increase in the sensed density being attributed to an increase in the solids fraction. After the water and solids fractions are determined, the remainder is attributed to the oil fraction.

The processing system 27 may also include an input/output (I/O) port 48 for provided data to or receiving information from an I/O device 28. The data can include calculated fractions, other data related to sensing the various fractions such as data from the various sensors, or alerts. Non-limiting embodiments of the I/O device 28 include a monitor, a printer, a keyboard, and a mouse. Alternatively or in addition, the I/O port 48 may be connected to a computer processing system (represented by the I/O device 28) disposed either locally or remotely to the sensor 12. In embodiments implementing Method 1 and Method 2, the processing system 27 can compare the fractions determined by each method. In one or more embodiments, if the difference between any two of the same fractional component determined by the two methods exceeds a selected threshold value, then an alert signal can be displayed to a user such as by a display monitor connected to I/O port 48 of the processing system 27. The alert signal can be an indication to the user that one or more components may not be functioning properly. The selected threshold value can be input into the processing system 27 using the I/O port 48 and the I/O device 28.

The processing system 27 may also include communication components and be configured to enable the processing system 27 to communicate determined fractions with a remote computer processing system such as by over the internet.

FIG. 3 is a flow chart representation for a method 30 for estimating fractions of components of a drilling fluid. Block 31 calls for containing the drilling fluid in a conduit. In one or more embodiments, the drilling fluid flows continuously in the conduit while properties of the drilling fluid are being sensed. Block 32 calls for sensing a combined water and solid fraction in the drilling fluid using an electromagnetic sensor in electromagnetic communication with the drilling fluid in the conduit. In one or embodiments, sensing a combined water and solid fraction in the drilling fluid includes inducing eddy currents in the drilling fluid by generating current in a coil wrapped around the conduit and measuring an energy loss due to the eddy currents, the energy loss being correlated to a combined water and solids fraction. Block 33 calls for sensing a water fraction of the drilling fluid using at least one of a conductivity sensor in communication with the drilling fluid in the conduit or a density sensor in communication with the drilling fluid in the conduit. In one or more embodiments, using a conductivity sensor includes sensing a conductivity value the drilling fluid such as by, for example, emitting a microwave signal into the drilling fluid, receiving a return signal, determining an amplitude and/or phase difference between the emitted signal and the return signal, and correlating the amplitude and/or phase difference to the conductivity value. The method 30 may also include converting the conductivity value to the water fraction. In one or more embodiments, using a density sensor includes sensing a density value of the drilling fluid such as by, for example, using a Coriolis sensor in communication with the drilling fluid to determine a change in density of the drilling fluid from a known initial value. Block 34 calls for determining the fractions of oil, water, and solids in the drilling fluid using the combined water and solids fraction and the water fraction. In one or more embodiments, only the combined water and solids fraction and the water fraction are used to determine the oil, water, and solids fractions. Block 35 calls for controlling an additive to be added to the drilling fluid based upon the fractions of oil, water, and solids in the drilling fluid.

The method 30 may also include receiving initial component fractions for the oil, water, and solids and an initial density value of the drilling fluid. The method 30 may further include determining a change in the density value from the initial density value, attributing a change in the combined water and solids fraction to a change in the water fraction in response to a decrease in the density value with respect to the initial density value, determining the solids fraction by subtracting the current water fraction from the combined water and solids fraction, and determining the oil fraction as the remainder making up the drilling fluid. The method 30 may further include determining a change in the density value from the initial density value, attributing a change in the combined water and solids fraction to a change in the solids fraction in response to an increase in the density value with respect to the initial density value, determining the solids fraction by subtracting the water fraction from the combined water and solids fraction, and determining the oil fraction as the remainder making up the drilling fluid.

The method 30 may further include sensing the combined water and solid fraction, the conductivity value, and the density value; determining first fractions of the oil, water, and solids using the combined water and solids fraction and the conductivity value and second fractions of the oil, water, and solids using the combined water and solid fraction and the density value; and sending a user an alert signal in response to a difference between the first fraction components and the second fraction components exceeding a threshold value.

The apparatuses and methods disclosed herein provide several advantages. One advantage is that the fractions of oil, water and solids are determined in real time, which can avoid excessive waste due to increased lag times associated with other methods. Another advantage is that using a retort method and the associated high temperature to determine the fractions can be avoided along with required personnel. In that fewer workers are required, there is significant cost savings and less congestion on a drilling rig. Yet another advantage is that displacement from one type of drilling fluid to another type of drilling fluid can be determined in less time thus eliminating wasted product.

In support of the teachings herein, various analysis components may be used, including a digital and/or an analog system. For example, the processing system 27, the electronics 22, 24 and 26, and the controller 14 may include digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the apparatus and methods disclosed herein in any of several manners well-appreciated in the art. Digital and/or analog processors may include a mathematics module or software for performing mathematical operations and analytical operations discussed in the disclosure herein. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply, magnet, electromagnet, sensor, electrode, transmitter, receiver, transceiver, antenna, controller, optical unit or components, electrical unit or electromechanical unit may be included in support of the various aspects discussed herein or in support of other functions beyond this disclosure.

Set forth below are some embodiments of the foregoing disclosure:

Embodiment 1: An apparatus for estimating a fraction of oil, water, and solids of a drilling fluid, the apparatus including a conduit containing the drilling fluid, an electromagnetic sensor in electromagnetic communication with the drilling fluid in the conduit, the electromagnetic sensor comprising a coil and electronics coupled to the coil, the electronics generating current in the coil inducing eddy currents in the drilling fluid and measuring an energy loss due to the eddy currents, the energy loss being correlated to a combined water and solids fraction, at least one of (i) a conductivity sensor comprising electronics coupled to a conductivity probe in conductive communication with the drilling fluid to provide a conductivity value or (ii) a density sensor comprising electronics coupled to a Coriolis sensor in communication with the drilling fluid to provide a density value, a processing system determining the fraction of oil, water, and solids in the drilling fluid using the combined water and solid fraction and at least one of the conductivity value from the conductivity sensor or the density value from the density sensor, the processing system having a first input coupled to the electromagnetic sensor, at least one of a second input coupled to the conductivity sensor or a third input coupled to the density sensor, and an output providing the fraction of oil, water, and solids, and a controller coupled to the output of the processing system, the controller having an output coupled to a drilling fluid additive control device controlling an additive to be added to the drilling fluid based on the fraction of oil, water, and solids of the drilling fluid.

Embodiment 2: The apparatus as in any prior embodiment, further comprising a housing containing the conduit, the electromagnetic sensor and at least one of the conductivity sensor or the density sensor.

Embodiment 3: The apparatus as in any prior embodiment, wherein the processing system is further disposed in the housing.

Embodiment 4: The apparatus as in any prior embodiment, wherein the processing system converts the conductivity value to a water fraction using a conversion factor, determines the solids fraction by subtracting the water fraction from the combined water and solids fraction, and determines the oil fraction as the remainder making up the drilling fluid.

Embodiment 5: The apparatus as in any prior embodiment, wherein the processing system comprises an input/output (I/O) port configured to receive initial component fractions for the oil, water, and solids and an initial density value of the drilling fluid.

Embodiment 6: The apparatus as in any prior embodiment, wherein the processing system is configured to attribute a change in the combined water and solids fraction to a change in the water fraction from the initial water fraction in response to a decrease in the density value, determine the solids fraction by subtracting the current water fraction from the combined water and solids fraction, and determine the oil fraction as the remainder making up the drilling fluid.

Embodiment 7: The apparatus as in any prior embodiment, wherein the processing system is configured to attribute a change in the combined water and solids fraction to a change in the solids fraction from the initial solids fraction in response to an increase in the density value, determine the solids fraction by subtracting the water fraction from the combined water and solids fraction, and determine the oil fraction as the remainder making up the drilling fluid.

Embodiment 8: The apparatus as in any prior embodiment, wherein the processing system is configured to receive data from the electromagnetic sensor, the conductivity sensor, and the density sensor and to determine first fractions of the oil, water, and solids using the data from the electromagnetic sensor and data from the conductivity sensor and second fractions of the oil, water, and solids using the data from the electromagnetic sensor and data from the density sensor.

Embodiment 9: The apparatus as in any prior embodiment, wherein the processing system is configured to determine a difference between the first fraction components and the second fraction components and provide an alert signal in response to the difference exceeding a threshold value.

Embodiment 10: The apparatus as in any prior embodiment, wherein the drilling fluid additive control device comprises one of a flow control valve or a metering pump.

Embodiment 11: The apparatus as in any prior embodiment, wherein the drilling fluid flows continuously through the conduit while being sensed.

Embodiment 12: A method for estimating an oil, water, and solids fraction of a drilling fluid, the method including containing the drilling fluid in a conduit, sensing a combined water and solid fraction in the drilling fluid using an electromagnetic sensor in electromagnetic communication with the drilling fluid in the conduit, sensing a water fraction of the drilling fluid using a conductivity sensor in communication with the drilling fluid in the conduit or a density value of the drilling fluid using a density sensor in communication with the drilling fluid in the conduit, determining the fraction of oil, water, and solids in the drilling fluid using the combined water and solid fraction and the water fraction, and controlling an additive to be added to the drilling fluid based upon the fraction of oil, water, and solids in the drilling fluid.

Embodiment 13: The method as in any prior embodiment, wherein sensing a combined water and solid fraction in the drilling fluid comprises inducing eddy currents in the drilling fluid by generating current in a coil wrapped around the conduit and measuring a power energy loss due to the eddy currents, the power energy loss being correlated to a combined water and solids fraction.

Embodiment 14: The method as in any prior embodiment, wherein sensing a conductivity value the drilling fluid comprises emitting a microwave signal into the drilling fluid, receiving a return signal, determining an amplitude and/or phase difference between the emitted signal and the return signal, and correlating the amplitude and/or phase difference to the conductivity value.

Embodiment 15: The method as in any prior embodiment, further comprising converting the conductivity value to the water fraction.

Embodiment 16: The method as in any prior embodiment, wherein sensing a density value comprises using a Coriolis sensor in communication with the drilling fluid.

Embodiment 17: The method as in any prior embodiment, wherein the method further comprises receiving initial component fractions for the oil, water, and solids and an initial density value of the drilling fluid.

Embodiment 18: The method as in any prior embodiment, wherein the method further comprises determining a change in the density value from the initial density value, attributing a change in the combined water and solids fraction to a change in the water fraction in response to a decrease in the density value with respect to the initial density value, determining the solids fraction by subtracting the current water fraction from the combined water and solids fraction, and determining the oil fraction as the remainder making up the drilling fluid.

Embodiment 19: The method as in any prior embodiment, wherein the method further comprises determining a change in the density value from the initial density value, attributing a change in the combined water and solids fraction to a change in the solids fraction in response to an increase in the density value with respect to the initial density value, determining the solids fraction by subtracting the water fraction from the combined water and solids fraction, and determining the oil fraction as the remainder making up the drilling fluid.

Embodiment 20: The method as in any prior embodiment, wherein the method comprises: sensing the combined water and solid fraction, the conductivity value, and the density value; determining first fractions of the oil, water, and solids using the combined water and solids fraction and the conductivity value and second fractions of the oil, water, and solids using the combined water and solid fraction and the density value; and sending a user an alert signal in response to a difference between any of the first fraction components and the corresponding second fraction components exceeding a threshold value.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates to one or more structural limitations of a device that are required for the device to perform the function or operation for which the device is configured. The limitations may be known in the art for a specific item, but not known in the context of or application to the invention as a whole. The limitations may be inclusive of circuit modules and software known to perform a specific function. The term "coupled" relates to being coupled directly or indirectly using an intermediate device. The terms "first" and "second" and like are used to distinguish terms and not to denote a particular order.

The flow diagram depicted herein is just an example. There may be many variations to this diagram or the steps (or operations) described therein without departing from the scope of the invention. For example, operations may be performed in another order or other operations may be performed at certain points without changing the specific disclosed sequence of operations with respect to each other. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. An apparatus for estimating a fraction of oil, water, and solids of a drilling fluid, the apparatus comprising:

a conduit containing the drilling fluid;

an electromagnetic sensor in electromagnetic communication with the drilling fluid in the conduit, the electromagnetic sensor comprising a coil and electronics coupled to the coil, the electronics generating current in the coil inducing eddy currents in the drilling fluid and measuring an energy loss due to the eddy currents, the energy loss being correlated to a combined water and solids fraction;

a conductivity sensor comprising electronics coupled to a conductivity probe in conductive communication with the drilling fluid to provide a conductivity value;

a density sensor comprising electronics coupled to a Coriolis sensor in communication with the drilling fluid to provide a density value;

a processing system determining the fraction of oil, water, and solids in the drilling fluid using the combined water and solid fraction and at least one of the conductivity value from the conductivity sensor or the density value from the density sensor, the processing system having a first input coupled to the electromagnetic sensor, at least one of a second input coupled to the conductivity sensor or a third input coupled to the density sensor, and an output providing the fraction of oil, water, and solids, wherein the processing system comprises an input port configured to receive initial component fractions for the oil, water, and solids and an initial density value of the drilling fluid; and a controller coupled to the output of the processing system, the controller having an output coupled to a drilling fluid additive control device controlling an additive to be added to the drilling fluid based on the fraction of oil, water, and solids of the drilling fluid;

wherein the processing system is configured to at least one of: (i) to attribute a change in the combined water and solids fraction to a change in the water fraction from the initial water fraction in response to a decrease in the density value, determine the solids fraction by subtracting the current water fraction from the combined water and solids fraction, and determine the oil fraction as the remainder making up the drilling fluid; or (ii) to attribute a change in the combined water and solids fraction to a change in the solids fraction from the initial solids fraction in response to an increase in the density value, determine the solids fraction by subtracting the water fraction from the combined water and solids fraction, and determine the oil fraction as the remainder making up the drilling fluid.

2. The apparatus according to claim 1, further comprising a housing containing the conduit, the electromagnetic sensor and at least one of the conductivity sensor or the density sensor.

3. The apparatus according to claim 2, wherein the processing system is further disposed in the housing.

4. The apparatus according to claim 1, wherein the processing system converts the conductivity value to a water fraction using a conversion factor, determines the solids fraction by subtracting the water fraction from the combined water and solids fraction, and determines the oil fraction as the remainder making up the drilling fluid.

5. The apparatus according to claim 1, wherein the drilling fluid additive control device comprises one of a flow control valve or a metering pump.

6. The apparatus according to claim 1, wherein the drilling fluid flows continuously through the conduit while being sensed.

7. A method for estimating an oil, water, and solids fraction of a drilling fluid, the method comprising:
  containing the drilling fluid in a conduit;
  sensing a combined water and solid fraction in the drilling fluid using an electromagnetic sensor in electromagnetic communication with the drilling fluid in the conduit;
  sensing a water fraction of the drilling fluid using a conductivity sensor in communication with the drilling fluid in the conduit or a density value of the drilling fluid using a density sensor in communication with the drilling fluid in the conduit;
  determining the fraction of oil, water, and solids in the drilling fluid using the combined water and solid fraction and the water fraction; and
  controlling an additive to be added to the drilling fluid based upon the fraction of oil, water, and solids in the drilling fluid;
  wherein the method further comprises receiving initial component fractions for the oil, water, and solids and an initial density value of the drilling fluid and at least one of: (i) determining a change in the density value from the initial density value, attributing a change in the combined water and solids fraction to a change in the water fraction in response to a decrease in the density value with respect to the initial density value, determining the solids fraction by subtracting the current water fraction from the combined water and solids fraction, and determining the oil fraction as the remainder making up the drilling fluid; or (ii) determining a change in the density value from the initial density value, attributing a change in the combined water and solids fraction to a change in the solids fraction in response to an increase in the density value with respect to the initial density value, determining the solids fraction by subtracting the water fraction from the combined water and solids fraction, and determining the oil fraction as the remainder making up the drilling fluid.

8. The method according to claim 7, wherein sensing a combined water and solid fraction in the drilling fluid comprises inducing eddy currents in the drilling fluid by generating current in a coil wrapped around the conduit and measuring a power energy loss due to the eddy currents, the power energy loss being correlated to a combined water and solids fraction.

9. The method according to claim 7, wherein sensing a conductivity value the drilling fluid comprises emitting a microwave signal into the drilling fluid, receiving a return signal, determining an amplitude and/or phase difference between the emitted signal and the return signal, and correlating the amplitude and/or phase difference to the conductivity value.

10. The method according to claim 7, further comprising converting the conductivity value to the water fraction.

11. The method according to claim 7, wherein sensing a density value comprises using a Coriolis sensor in communication with the drilling fluid.

12. An apparatus for estimating a fraction of oil, water, and solids of a drilling fluid, the apparatus comprising:
  a conduit containing the drilling fluid;
  an electromagnetic sensor in electromagnetic communication with the drilling fluid in the conduit, the electromagnetic sensor comprising a coil and electronics coupled to the coil, the electronics generating current in the coil inducing eddy currents in the drilling fluid and measuring an energy loss due to the eddy currents, the energy loss being correlated to a combined water and solids fraction;
  a conductivity sensor comprising electronics coupled to a conductivity probe in conductive communication with the drilling fluid to provide a conductivity value;
  a density sensor comprising electronics coupled to a Coriolis sensor in communication with the drilling fluid to provide a density value;
  a processing system determining the fraction of oil, water, and solids in the drilling fluid using the combined water and solid fraction and at least one of the conductivity value from the conductivity sensor or the density value from the density sensor, the processing system having a first input coupled to the electromagnetic sensor, at least one of a second input coupled to the conductivity sensor or a third input coupled to the density sensor, and an output providing the fraction of oil, water, and solids; and
  a controller coupled to the output of the processing system, the controller having an output coupled to a drilling fluid additive control device controlling an additive to be added to the drilling fluid based on the fraction of oil, water, and solids of the drilling fluid;
  wherein the processing system is configured to receive data from the electromagnetic sensor, the conductivity sensor, and the density sensor and to determine first fractions of the oil, water, and solids using the data from the electromagnetic sensor and data from the conductivity sensor and second fractions of the oil, water, and solids using the data from the electromagnetic sensor and data from the density sensor.

13. The apparatus according to claim 12, wherein the processing system is configured to determine a difference between the first fraction components and the second fraction components and provide an alert signal in response to the difference exceeding a threshold value.

14. A method for estimating an oil, water, and solids fraction of a drilling fluid, the method comprising:
  containing the drilling fluid in a conduit;
  sensing a combined water and solid fraction in the drilling fluid using an electromagnetic sensor in electromagnetic communication with the drilling fluid in the conduit;
  sensing a water fraction of the drilling fluid using a conductivity sensor in communication with the drilling fluid in the conduit and a density value of the drilling fluid using a density sensor in communication with the drilling fluid in the conduit;

determining the fraction of oil, water, and solids in the drilling fluid using the combined water and solid fraction and the water fraction; and controlling an additive to be added to the drilling fluid based upon the fraction of oil, water, and solids in the drilling fluid;

wherein the method further comprises: determining first fractions of the oil, water, and solids using the combined water and solids fraction and the conductivity value and second fractions of the oil, water, and solids using the combined water and solids fraction and the density value; and sending a user an alert signal in response to a difference between any of the first fraction components and the corresponding second fraction components exceeding a threshold value.

* * * * *